United States Patent [19]

Karp

[11] 4,131,427
[45] Dec. 26, 1978

[54] CHROMATOGRAPHY DETECTOR

[76] Inventor: Stewart Karp, 15 Field La., Roslyn Heights, N.Y. 11577

[21] Appl. No.: 877,489

[22] Filed: Feb. 13, 1978

Related U.S. Application Data

[63] Continuation-in-part of Ser. No. 767,647, Feb. 10, 1977, abandoned.

[51] Int. Cl.² ............... G01N 31/08; G01N 21/46; G01N 21/26
[52] U.S. Cl. .................. 23/230 R; 73/61.1 C; 210/31 C; 356/129; 422/55; 422/69
[58] Field of Search ............ 23/230 R, 253 R; 73/61.1 C; 356/129, 105

[56] References Cited

U.S. PATENT DOCUMENTS

| 3,996,004 | 12/1976 | Fine | 73/61.1 C X |
| 4,014,793 | 3/1977 | Tesarik | 23/253 R X |
| 4,019,372 | 4/1977 | Parkell | 73/61.1 C |
| 4,036,704 | 7/1977 | Takata | 23/230 R |

OTHER PUBLICATIONS

Chemical Abstracts, 79:93813m (1973).
L. R. Snyder et al., Intro. to Modern Liquid Chromatog., 135–167, John Wiley & Sons, New York, 1974.
M. Bakken et al., J. Chromatos. Sci., 9, 603–606 (Oct. 1971).
Chemical Abstracts, 76:79229g (1972).
Chemical Abstracts, 79:48961x (1973).

*Primary Examiner*—Sidney Marantz

[57] ABSTRACT

A means for detecting the presence of a solute in a flowing fluid stream is disclosed within. The schlieren patterns obtained when a solute present in a flowing fluid stream is directed into a reference fluid stream are utilized to scatter a portion of a light beam. The scattered light is detected and is related to the presence and amount of solute.

2 Claims, 1 Drawing Figure

CHROMATOGRAPHY DETECTOR

DISCLOSURE

Cross Reference to Related Application

This application is a continuation-in-part of application Ser. No. 767,647 which was filed on Feb. 10, 1977, abandoned by the same inventor.

BACKGROUND OF THE INVENTION

The present invention relates to detecting the presence of a solute in a flowing fluid stream, herein called a carrier stream, upon the emergence of said carrier stream from a chromatographic column. More specifically, it relates to a detector for use in liquid chromatography. Liquid chromatography detectors are the subject of numerous patents, for example, Juvet et. al. U.S. Pat. No. 3,902,848, Broerman U.S. Pat. No. 3,513,319, Tesarik and Krejci U.S. Pat. No. 4,014,793, and Parkell and Stamm U.S. Pat. No. 4,019,372 and many publications, for example, L. R. Snyder, et. al., "Introduction to Modern Liquid Chromatography," John Wiley and Sons, New York, 1974.

An ideal detector will be both sensitive to small amounts of solute in the carrier stream and "universal" in that it can detect many types of compounds in the carrier stream. Detection based upon the absorption or emission (fluorescence) of light by the solute can be very sensitive, however, since each compound has its unique absorption and fluorescence spectrum, such detectors are not "universal". A frequently employed approach to designing a "universal" detector involves evaporating the carrier stream, i.e., the solvent, and then detecting the solute by some means such as for example, flame ionization. Such detectors can be quite "universal" and sensitive, but they are complex. Refractive index detectors are available and they are "universal" but very insensitive.

SUMMARY OF THE INVENTION

The herein described invention utilizes the difference in density and refractive index of the solute in the carrier stream relative to the pure carrier stream in a manner which very sensitively and "universally" provides an optical signal which is related to the amount of solute present. The present invention detects the solute in the carrier stream by combining the carrier stream emerging from the chromatographic column with another fluid stream, herein called the reference stream, which is identical to the carrier stream except for the absence of a solute. The presence of a solute in the carrier stream, upon mixing with the reference stream, causes schlieren to appear, i.e., the formation of regions of different density and refractive index. The extent of the schlieren, the differences in density and refractive index, is a function of the concentration of the solute in the carrier stream. The presence of these schlieren are detected by passing a well collimated beam of light through the region at which the schlieren appear. When schlieren are present, i.e., when a solute has reached the place of mergence of the two flowing streams, the light beam will be refracted and reflected from the regions of differing density and refractive index. Hence, some portion of the intensity of the light beam will be effectively scattered as it passes through the schlieren pattern, the extent of this scattering being a function of the concentration of the solute. The scattered light is detected by a light sensitive device placed so that the unscattered light beam does not reach the light sensitive device. The signal from the light sensitive device is monitored by an appropriate electrical circuit. The signal is a function of the presence and concentration of solute in the carrier stream. State of art light sensitive devices and electrical circuits applicable for the present purpose are well known.

DETAILED DESCRIPTION OF THE INVENTION

Figure 1:
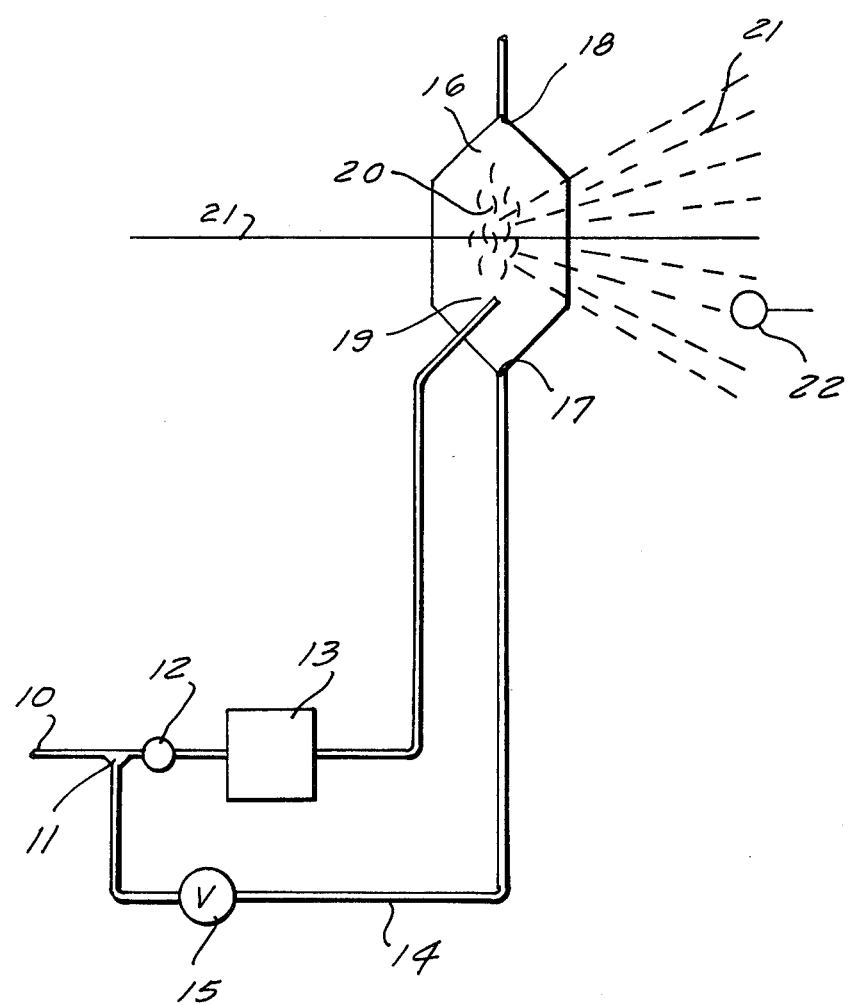
FIG. 1 is a schematic diagram illustrating a preferred embodiment of the invention.

The present invention will be more fully appreciated by reference to the following detailed description of a presently preferred but nonetheless illustrative embodiment of the invention, wherein FIG. 1 is a diagrammatic illustration of it. With reference to FIG. 1, the carrier stream consisting of any of the solvents generally used in liquid chromatography such as, but not limited to, water, methanol and isooctane, enters, 10, from a conventional liquid chromatographic pumping-resevoir system. A splitter, 11, of conventional design, divides the flow in part to a sample injection port, 12, which consists of a rubber septum of the type generally found on liquid chromatographs, and thence to the chromatographic column, 13; and in part to the reference stream tubing, 14. The reference stream flow is controlled by an adjustor, 15, which is a device, in the present case a needle valve, which can optimize the flow of the reference stream. The reference stream enters the cell, 16 at the entry point, 17 and its flow continues out the exit point, 18, thereby flushing the entire cell. In the described embodiment the cell is a glass cylinder approximately 1cm. long and 0.5 cm. i.d. It is sealed at both ends except for the glass tubing at the two ends, 17 and 18. The carrier stream enters the cell by means of a small tube sealed through the cell wall, 19, and this stream thereby mixes with the reference stream. The material and dimensions are not limited to those herein described as many variations and modifications will now occur to those skilled in the art. A solute present in the carrier stream will cause schlieren patterns to appear, 20. Examples of detectable solutes which may be cited are inorganic compounds such as, but not limited to, nickel chloride, ferric chloride and cupric chloride all in an aqueous carrier stream; and organic compounds such as, but not limited to, carbon tetrachloride, benzene and napthalene in an isooctane carrier stream. A well collimated light beam, 21, is directed through the cell at the region where the maximum amount of schlieren, 20, are present. The scattered light, 21, is detected by the light sensitive device, 22. This light sensitive device is placed at the position which is optimum for detecting the scattered light. Methods for collimating light beams and for detecting light are well known to those skilled in the art and typical methods are used in the present embodiment.

An electrical signal from the light sensitive device, 22, is in the usual application, recorded by a system of which many are well known and readily available. Said electrical signal will result upon the appearance of a solute in the cell, 16, and the magnitude of said signal will be a function of the concentration of the solute. Precise quantitative evaluation of the amount of solute is performed by the well known procedure of comparing the signal resulting from an unknown sample with that of a known sample.

What is claimed is:

1. A method for detecting and determining the quantity of a solute present in the carrier stream which emerges from a chromatographic column which comrises: directing said carrier stream into a mixing cell in which said carrier stream mixes with a reference stream thereby causing the appearance of schlieren when said solute is present in said carrier stream; directing a light beam through said cell to detect the schlieren, thereby causing the change of direction of some portion of said light beam when said solute is present in said carrier stream; and detecting some or all of said light which had changed direction.

2. An apparatus for detecting and determining the quantity of a solute present in the carrier stream which emerges from a chromatographic column which comprises; a means for directing said carrier stream into a mixing cell in which said carrier stream mixes with a reference stream thereby causing the appearance of schlieren when said solute is present in said carrier stream; a means for directing a light beam through said cell to detect said schlieren, thereby causing the change of direction of some position of said light beam when said solute is present in said carrier stream; and a means for detecting some or all of said light which had changed direction.

* * * * *